(12) United States Patent
Scheyer

(10) Patent No.: US 7,695,432 B2
(45) Date of Patent: Apr. 13, 2010

(54) INSTRUMENT FOR USE IN THE TREATMENT OF PROLAPSED HEMORRHOIDS

(75) Inventor: Mathias Scheyer, Feldkirch (AT)

(73) Assignee: AMI Agency for Medical Innovations GmbH, Feldkirch (AT)

( * ) Notice: Subject to any disclaimer, the term of this patent is extended or adjusted under 35 U.S.C. 154(b) by 448 days.

(21) Appl. No.: 11/338,650

(22) Filed: Jan. 25, 2006

(65) Prior Publication Data

US 2006/0167473 A1 Jul. 27, 2006

(30) Foreign Application Priority Data

Jan. 25, 2005 (AT) ............... A 108/2005
Sep. 2, 2005 (AT) ............... A 1438/2005

(51) Int. Cl.
*A61B 1/31* (2006.01)
(52) U.S. Cl. ....................... 600/184; 606/148
(58) Field of Classification Search ........... 606/104, 606/105, 114, 184, 139–148, 197–198; 600/104, 600/105, 114, 184, 128, 135–138
See application file for complete search history.

(56) References Cited

U.S. PATENT DOCUMENTS

| | | | | |
|---|---|---|---|---|
| 295,798 | A * | 3/1884 | Pagett | 600/184 |
| 5,025,778 | A * | 6/1991 | Silverstein et al. | 600/104 |
| 5,570,692 | A * | 11/1996 | Morinaga | 600/453 |
| 6,126,594 | A * | 10/2000 | Bayer | 600/184 |
| 6,142,931 | A * | 11/2000 | Kaji | 600/114 |
| 6,142,933 | A * | 11/2000 | Longo et al. | 600/184 |
| 6,632,227 | B2 * | 10/2003 | Adams | 606/110 |
| 2003/0130559 | A1 * | 7/2003 | Morin et al. | 600/104 |
| 2006/0036129 | A1 * | 2/2006 | Sias | 600/135 |

FOREIGN PATENT DOCUMENTS

| | | |
|---|---|---|
| DE | 83 16 987 | 11/1983 |
| DE | 102 31 004 | 1/2004 |
| EP | 1 234 539 | 8/2002 |
| WO | 2004/064624 | 8/2004 |

* cited by examiner

*Primary Examiner*—(Jackie) Tan-Uyen T Ho
*Assistant Examiner*—Mark Mashack
(74) *Attorney, Agent, or Firm*—Wenderoth, Lind & Ponack, L.L.P.

(57) ABSTRACT

An instrument for use in the treatment of prolapsed hemorrhoids by applying a purse-string suture includes a tube, which has a distal end, with which it can be inserted forward into the rectum of a patient. The tube also has an open proximal end and a shell wall encompassing an inner hollow space and is provided with an elongated opening. The opening extends in the axial direction of the tube from a distal end to a proximal end. The instrument also includes a closure device, which in a closing position closes the opening and by which the opening can be successively exposed from the distal to the proximal end.

21 Claims, 7 Drawing Sheets

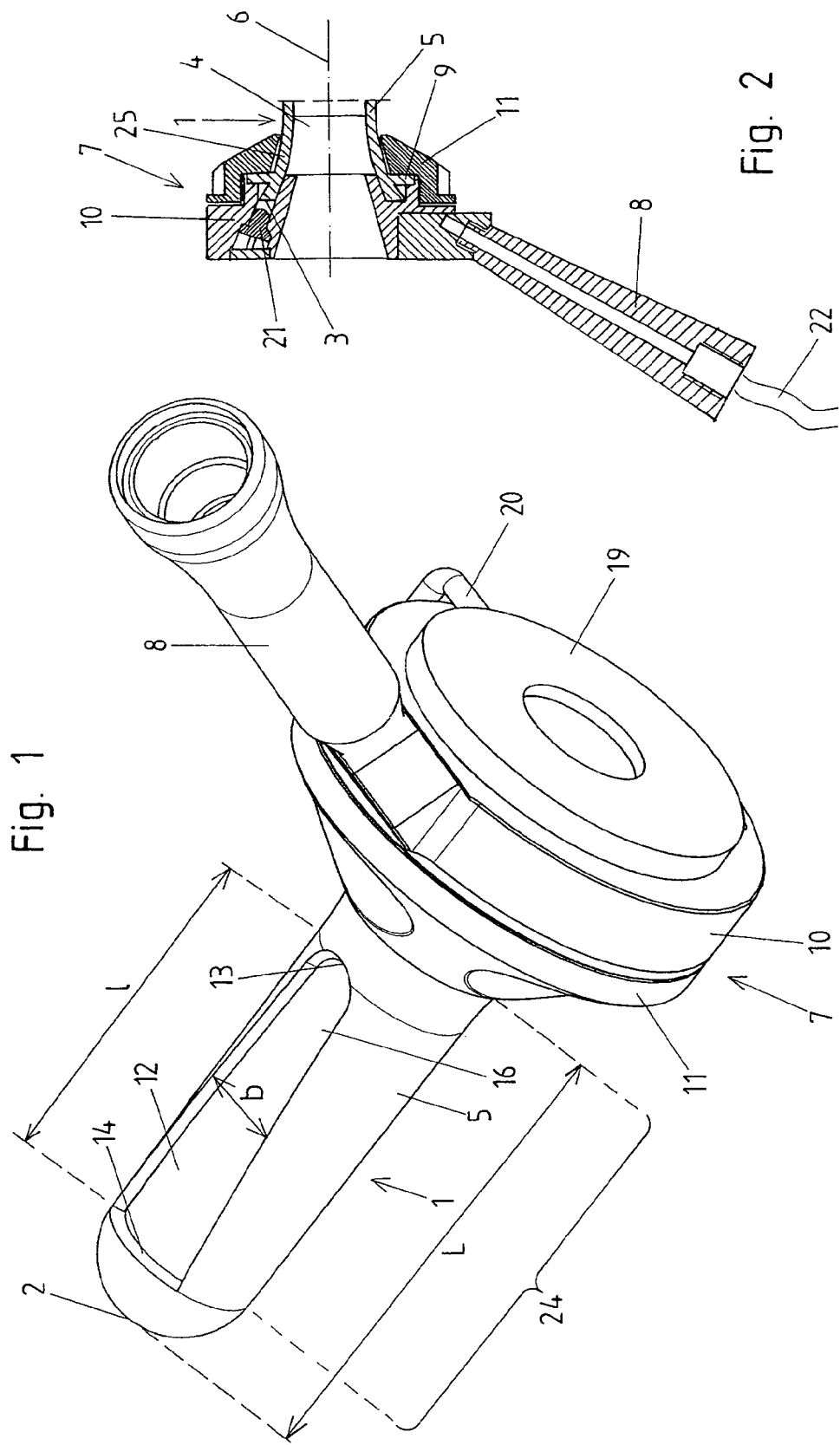

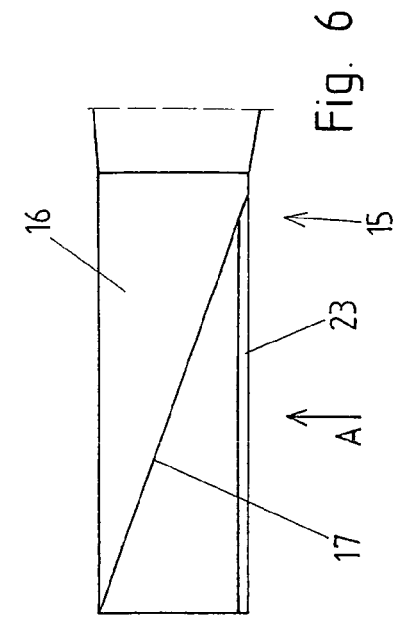
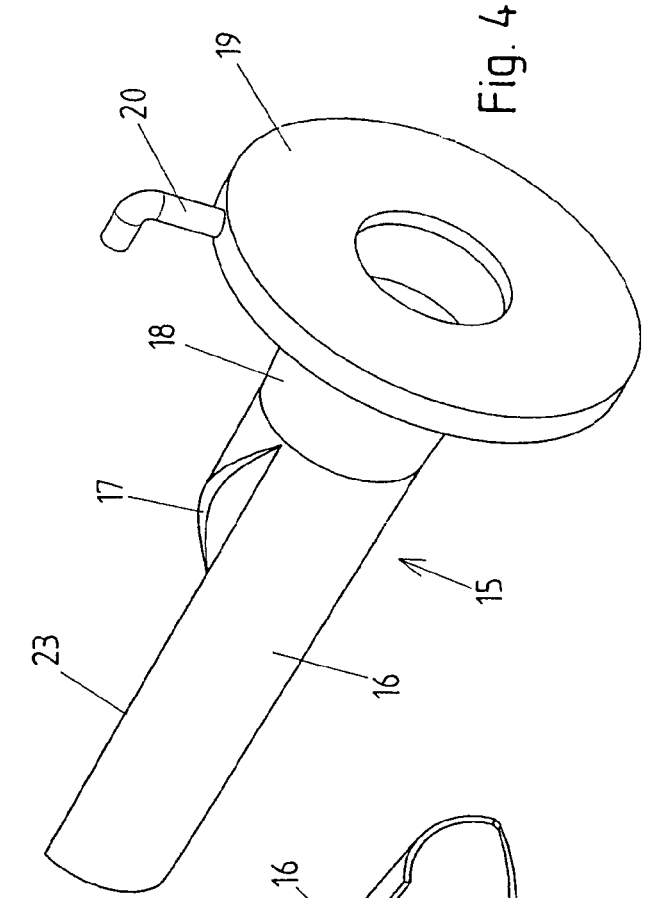
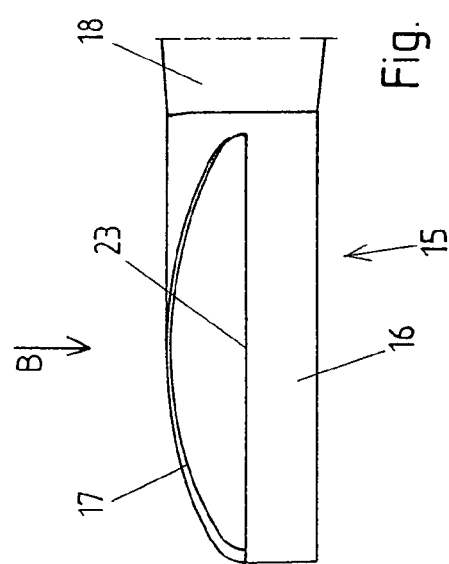
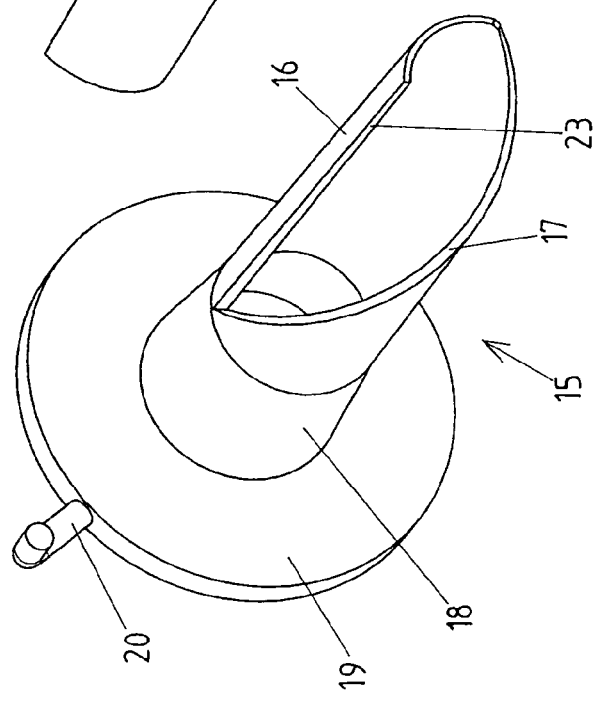

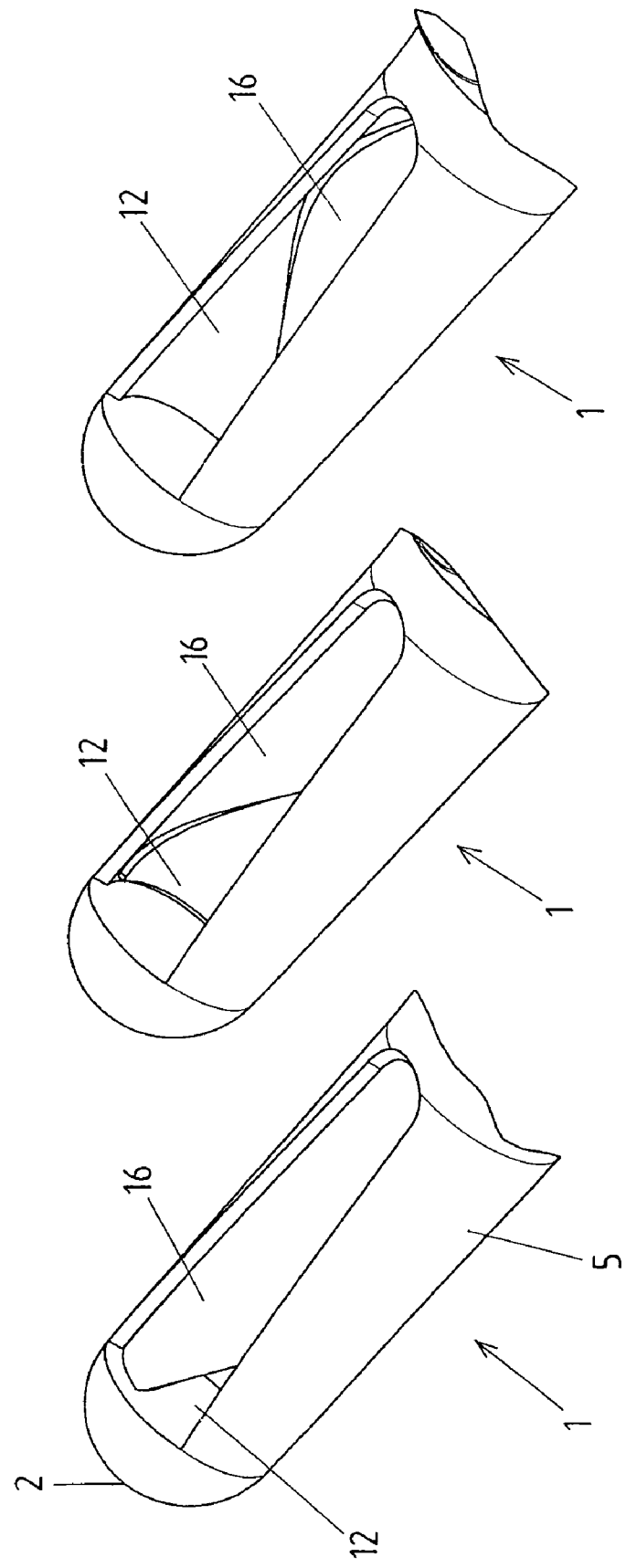

INSTRUMENT FOR USE IN THE TREATMENT OF PROLAPSED HEMORRHOIDS

BACKGROUND OF THE INVENTION a) Field of the Invention

The invention relates to an instrument for use in the treatment of prolapsed hemorrhoids by applying a continuous tightening and/or lifting suture.

b) Description of Related Prior Art

A known surgical method consists in making an incision in the anorectal transition zone and ligating the exposed hemorrhoidal arteries and furthermore removing enlarged hemorrhoids (prolapsed nodules). This operation is painful for patients, since it is performed in the anorectal transition zone which is sensitive to pain. In addition, this operation involves greater invasiveness and the disadvantages and risks associated therewith.

Also known is a minimally invasive hemorrhoidal artery ligature performed by means of an ultrasonic probe to be inserted into the rectum. An ultrasonic sensor is disposed in the distal region of a tube, specifically next to an opening in the shell wall of the tube. A hemorrhoidal artery running within the intestinal wall is located by means of the ultrasonic probe and subsequently ligature of the artery is carried out through the opening in the tube. Apart from the minimal invasiveness, one advantage of this treatment method frequently applied today is that the treatment takes place in the region of the intestinal wall above the dentate line and consequently not in a pain-sensitive area. However, this method frequently no longer yields the desired treatment results in the case of prolapsed hemorrhoids of degree III and IV. These degrees involve pronounced prolapsed hemorrhoidal cushions (=prolapsed nodules) or prolapsed mucosa, which prolapses from the anus more or less pronouncedly and more or less permanently. Such instruments for a hemorrhoid arterial ligation are disclosed for example in U.S. Pat. No. 5,570,692 A and EP 1 234 539 A2.

Isolated operations have already been performed in which the prolapsed nodules were drawn tight by means of purse-string sutures in order to decrease the prolapse considerably. However, these operations have been found to be technically difficult, since, depending on the findings, the prolapse of the mucosa makes precise and targeted piercing of the mucosa impossible in this region, and maintaining an adequate distance from the dentate line cannot be sufficiently controlled (pain is the consequence) and the time expenditure for the individual piercing steps is too high (most often it is necessary to pierce the mucosa four to five times in order to achieve the desired success). This surgical method has therefore not become widely used and is not part of any standard surgical procedure applied today.

SUMMARY OF THE INVENTION

The aim of the invention is providing an instrument with which applying a purse-string (continuous, tightening) suture of a hemorrhoidal prolapse is simplified and is, at least to a certain degree, standardized.

According to the invention this is achieved through an instrument comprising a tube having a distal end, which can be inserted forward into the rectum of a patient, an open proximal end and a shell wall encompassing an inner hollow space, which is provided with an elongated opening extending in the axial direction of the tube from the distal end up to the proximal end. The instrument also comprises a closure device, which in a closing position closes the opening and by which the opening can be exposed successively from the distal end toward the proximal end.

To apply a continuous, tightening suture, the tube of the instrument is inserted into the rectum, a stop being preferably provided which delimits the depth of insertion. The tube is rotated about its longitudinal axis so that its elongated opening extending in the direction of the longitudinal axis of the tube comes to lie in the area of the prolapse. The opening is initially closed by the closure device.

To complete the suture, a first distal section of the opening is exposed, with the mucosa of the prolapse protruding into the opening. In this area a first stitch of the continuous, tightening suture to be applied is completed. Subsequently a further section of the opening is exposed by means of the closure device, which section proximally adjoins the previously exposed section of the opening. In this proximally adjoining section a further piercing is now carried out. This process is repeated until the desired number of piercings has been carried out. As a result, a continuous and elongated tightening and/or lifting suture is applied. Each piercing can readily be monitored optically and the mucosa can be pierced at the desired distances from the anus. The risk of getting too close to the dentate line or beyond it in the direction toward the anus is hereby reduced. The piercings can also be completed simply and rapidly. The further tying of the suture can take place in a known manner.

For the illumination of the operating field an illuminating device is advantageously available.

In a first embodiment of the invention the closure device comprises a closure part disposed within the tube, which is formed by a portion of a shell of a hollow cylinder and which is rotatable with respect to the tube about the longitudinal axis of this hollow cylinder or of the tube. Depending on the rotational position of this closure part, a distal section of greater or lesser size of the opening in the shell wall of the tube is exposed or closed by the closure part.

In a second embodiment of the invention the closure device comprises a closure part encompassing the tube on the outside, which is formed by a portion of the shell of a hollow cylinder and which is rotatable with respect to the tube about the longitudinal axis of this hollow cylinder or of the tube. Again, depending on the rotational position of the closure part, a distal section of the elongated opening in the shell wall of the tube of greater or lesser size is exposed or the opening is closed.

In both embodiments of the invention an ultrasonic sensor can be disposed on the tube and the tube can be provided with a ligature opening. The instrument can consequently also be utilized for the ligation of intramural arteries. Such a ligature usually precedes the application of a continuous, tightening suture of the present invention. The ligature opening can advantageously also be closable and exposable by the closure device. The ligature opening can be formed as a separate opening in the tube or as a lateral expansion of the axial opening.

The terms distal and proximal in reference to the instrument according to the invention should be understood to mean that these are in reference to the side facing the surgeon, i.e. the distal end of the instrument is the insertion end of the tube and the proximal end is the opposite end of the instrument. On the other hand, in reference to the gastrointestinal tract, the terms proximal and distal denote the location relative to the mouth of the patient. The tube is consequently inserted into the distal rectum.

Within the scope of the present document, a hemorrhoidal prolapse denotes every prolapse of the mucosa of the distal rectum or the "cavernosum recti". In this document such prolapsed mucosa is also referred to as "mucosa prolapse", "prolapsed node", "prolapsed nodule", "prolapsed hemorrhoidal cushion" or "prolapsed extension".

In the following further advantages and details of the invention will be explained in conjunction with the attached drawing, on the basis of which further aims of the invention will also be evident.

BRIEF DESCRIPTION OF THE DRAWINGS

In the drawings:

FIG. 1 is an oblique view of a first embodiment of the invention, with the opening of the tube closed by the closure device, FIG. 2 shows a portion of an axial center section in the region of the proximal end of the tube and the mounting of the tube provided with the hand grip, without the closure device, FIG. 3 and FIG. 4 are oblique views of the closure device from different viewing directions, FIG. 5 is a schematic side view of a distal section of the closure device (direction of viewing A of FIG. 6), FIG. 6 is a side view of the section of the tube shown in FIG. 5, rotated by 90 degrees (direction of viewing B of FIG. 5), FIGS. 7 to 9 are oblique views of distal sections of the instrument according to this embodiment with the closure device in different positions.

DETAILED DESCRIPTION OF THE PREFERRED EMBODIMENTS

Figure 10:
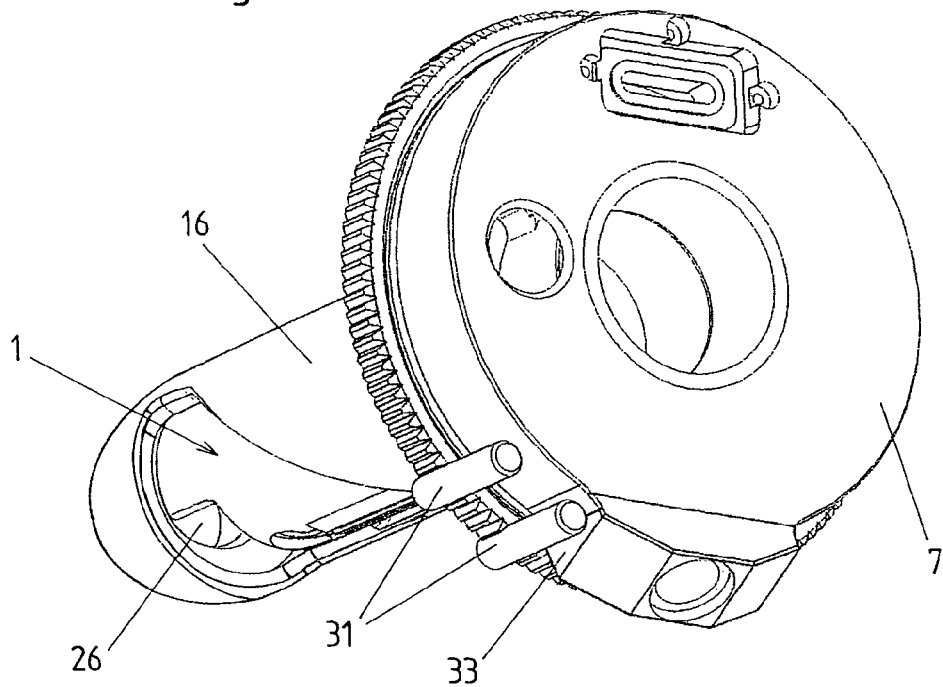
FIG. 10 and FIG. 11 are oblique views from obliquely behind and obliquely in front of a second embodiment of the invention, in the ligature position of the closure device (FIG. 10 shows the instrument without the hand grip and in FIG. 11 only a section of the hand grip is shown)
Figure 11:
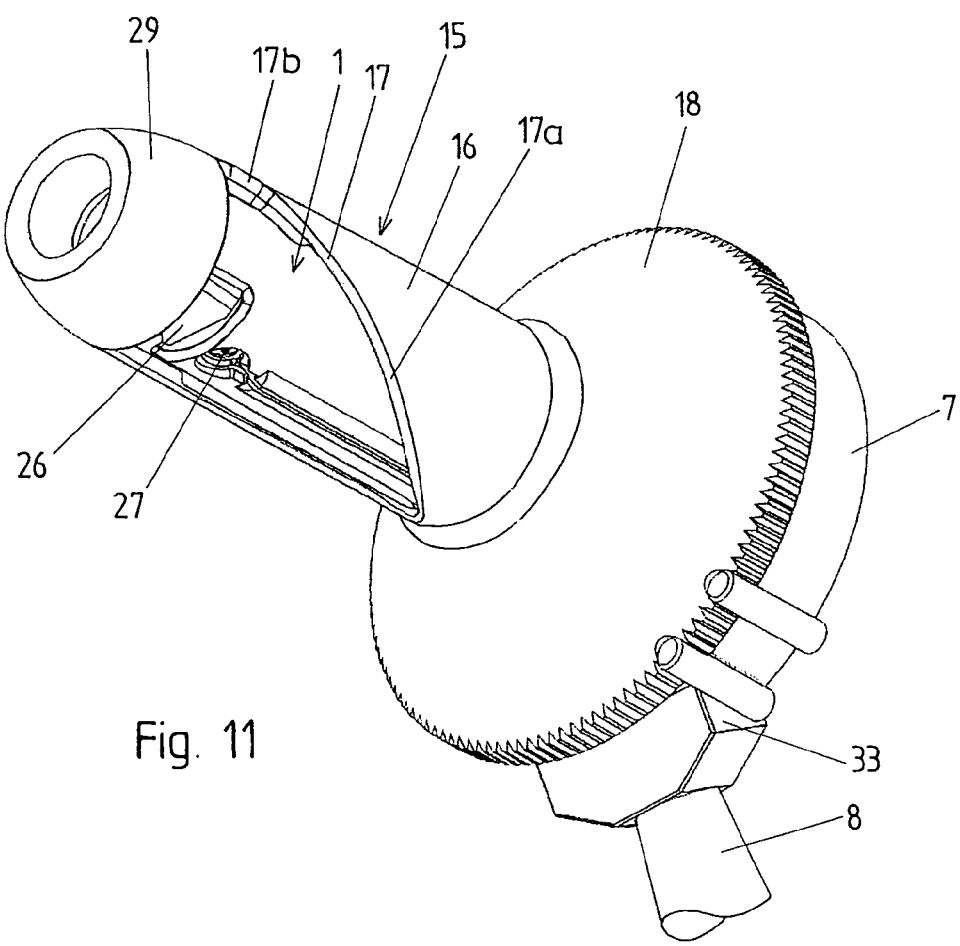

A first embodiment of an instrument according to the invention is depicted in FIGS. 1 to 9. The instrument comprises a tube 1 (=a sleeve). This tube 1 can be inserted with its distal end 2 through the anus of a patient into the rectum. In the depicted embodiment example the distal end of the tube 1 is developed such that it is closed. An open formation of the distal end 2 is also conceivable and possible. The proximal end 3 (cf. FIG. 2) of the tube 1 is developed such that it is open.

The tube 1 has a shell wall 5 encompassing the inner hollow space 4 of the tube 1. This shell wall has an annular form in cross section or is developed in the region, in which the opening 12, described later, is disposed, in the form of a circumferential segment of an annulus and encompasses the longitudinal axis 6 of tube 1.

Tube 1 has a cylindrical section 24 extending over the greater portion of its longitudinal extent. Adjoining it in the depicted embodiment example on the distal end of the tube is a rounded cap section and in the region of the proximal end is located a section 25 with increasing circumference (a flared section).

The tube 1 is disposed on a mounting portion 7, which includes a hand grip 8. For this purpose the tube 1 is set with a proximal flange 9 into a housing part 10 of the mounting portion 7. On part 10 outer threads are provided onto which a cap nut 11 can be screwed, which presses the flange 9 onto the housing part 10. Different means of fastening tube 1 on the mounting portion 7 or the formation of tube 1 integrally with mounting 7 are also conceivable and possible. The instrument may be sterilizable or be developed as a disposable instrument.

In the shell wall 5 an elongated opening 12 is formed extending in the direction of the longitudinal axis 6. This opening could also be described as an elongated hole or a slot. The opening 12 preferably extends at least over the greater portion of the length of tube 1. In the depicted embodiment it extends over the entire cylindrical section of tube 1.

The length/of opening 12 measured in the axial direction is preferably at least twice as large as its width b measured perpendicularly hereto. The length/of opening 12 is best in the range of 40 to 80 mm. Its width b is best in the range of 8 to 20 mm.

The width b of the opening can vary over its axial extent, and preferably decreases minimally in the proximal direction. For example its width b at the proximal end of opening 12 is 10% to 50% less than at the distal end 14 of opening 12.

The length L projecting beyond the mounting portion 7 of tube 1 is preferably in the range of 60 to 100 mm.

As shown in FIGS. 3-6, instrument further comprises a closure device 15, by which, in a closing position, the opening can be closed and by which the opening 12 can be exposed successively from the distal to the proximal end.

The closure device 15 has a closure part 16 formed by a portion of the shell of a hollow cylinder. The outer diameter of this hollow cylinder is only minimally smaller than the inner diameter of tube 1 in its cylindrical section, such that the closure part 16 can be slid with tolerance into the cylindrical section of tube 1 and is slip-guided in it. The tolerance (i.e. the difference between the outer diameter of the closure part and the inner diameter of tube 1 in its section encompassing the closure part) is best less than 1 mm, a value of less than 0.3 mm being preferred. When the closure part 16 is slid in, the closure part 16 and the tube 1 are coaxial.

The circumferential extent of the closure part 16 over the axial region, in which extends the opening 12, is at least as large as the circumferential extent of opening 12, preferably minimally greater.

The circumferential extent of the closure part 16 increases toward the proximal end 13 of opening 12. This increasing circumferential extent of the closure part is formed by an edge 17 of closure part 16 having the form of a section of an ellipse. Such an edge 17 is formed by a cut over a portion of the width of the diameter of the closure part, for example over half the diameter of the closure part 16, this cut extending obliquely with respect to the longitudinal axis of the closure part 16 (which coincides with the longitudinal axis 6 of the tube 1). This oblique cut line forming the edge 17 is most clearly evident in FIG. 6. This edge 17 could also be described as extending helically about the longitudinal axis of the closure part.

The other edge 23 of the closure part 16 extends in the axial direction.

The closure part 16 is connected at its proximal end to an expanding section 18, which in cross section is formed annularly, with an outwardly projecting annular flange 19 (this flange is a disk with a hole corresponding to the inner diameter of the closure part 16). On the outer edge of the annular flange a handle (a grip part) 20 is attached. The annular flange delimits the insertion of closure part 16 into tube 1 and, consequently, positions the closure part 16 in the axial direction with respect to tube 1. The handle 20 serves for rotating the closure part 1 with respect to tube 1 and its longitudinal axis 6.

In the rotational position of the closure part 16 with respect to tube 1 depicted in FIG. 1, the closure part 16 covers the opening 12 completely, i.e. the opening 12 is closed by the closure device 15. This is the closing position of the closure device 15. By rotating the closure part 16 by means of handle 20 in the clockwise direction, the opening 12, starting from the region of its distal end 14, is successively (i.e. gradually) exposed toward its proximal end 13, as is depicted in FIGS. 7 to 9. In an opening position or an exposing position of the closure device 15 the opening 12 is preferably completely exposed, as is shown in FIG. 9.

In the depicted embodiment example, starting from the closing position of the closure device 15, the opening 12 is consequently continuously exposable. It would also be conceivable and possible for the opening 12 to be exposed stepwise, for example through the corresponding formation of the edge 17 of closure part 16.

In the embodiment example according to FIGS. 1 to 9, the instrument comprises further, as is preferred, an illuminating device. For this purpose in part 10 several light-emitting diodes 21 are disposed spaced apart from one another in the circumferential direction of tube 1, which emit into the proximal end of the shell wall 5 of the tube. The power supply can be implemented, for example, by a cable 22 leading into the hand grip 8. The light supplied by the light-emitting diodes 21 into the shell wall 5 of the tube 1, the shell wall 5 being comprised of a translucent material, is conducted further in the shell wall 5 through total reflection. Desired exit sites for the light can be formed by roughing the inner surface of the shell wall in order to illuminate the surgical field in the region of opening 12. Other illuminating devices are also conceivable and possible and the light can be guided, for example, by means of one or several light guides in tube 1 up into the proximity of the site of the surgery. An external light source can also be provided from which light is introduced into the instrument through a light guide cable.

Before the hemorrhoid suture procedure described in the following (i.e., before the inventive procedure described below), a conventional hemorrhoid arterial ligature is usually applied in association with the inventive suture procedure, for example with the instruments disclosed in the above cited documents.

To carry out the suture procedure of the hemorrhoid, tube 1 is introduced through the anus into the rectum corresponding to the location of a prolapsed node to be ligated, such that opening 12 comes to lie in the area of the prolapse. Tube 1 can herein be inserted up to the cap nut 11, which forms a stop such that a defined insertion depth of the tube 1 is provided. During the insertion of tube 1 the closure device is initially in its closing position closing the opening 12.

Subsequently a distal section of the opening is exposed. Into this section of the opening a node section has prolapsed, which is remote from the anus and is to be tightened and/or lifted. Now for the first time the mucosa is pierced as deeply as is possible, and care must be taken that the suture thread does not become entangled. It has been found to be best to fix the rear end of the long suture (for example Vicryl20 thread) with a clamp and to carry it upwardly out of the tube.

Subsequently the opening is exposed further in steps from the distal to the proximal end, such that increasingly more of the mucosa of the node to be lifted protrudes into the opening 12 of tube 1, and each time, after a suitable distance, for example 1 cm, the mucosa is pierced again grasping as much tissue as possible. This is carried out until the entire opening 12 is exposed, wherein care must be taken that between the last stitch and the dentate line an adequate distance is maintained to prevent pain.

This continuous suture is subsequently tied in the conventional manner (as in conventional hemorrhoid arterial ligation) using a knot pusher. It has been found useful to push the tube 1 in the area of the prolapse slightly into the opposite direction in order to relieve the mucosa or the anal canal of stress. Herein the sliding up of the hemorrhoidal cushion while knotting the continuous suture is attained. Herein the lifting of the prolapse (hemorrhoidal cushion) into the anal canal normally occurs. Subsequently the continuous tightening and/or lifting ligature is tied and the thread cut in the conventional manner. Tube 1 is removed from the anus. If further hemorrhoidal cushions have prolapsed, the same procedure is applied to them.

During the hemorrhoidal tightening and/or lifting pursestringing the hemorrhoidal tissue is advantageously preserved, which has also a sealing function.

Different formations of a closure device are also conceivable and possible. For example, as the closure part a slider displaceable in the axial direction of the tube can be provided, which, in its end position, in which it is slid forward in the direction to the distal end of tube 1, completely covers the opening 12 and which can be retracted in the proximal direction of tube 1 for the continuous exposure of opening 12. However, such a closure device is less preferred due to the required greater overall length of the instrument. In another implementation of a closure device, several closure parts could, for example, be disposed one next to the other in the longitudinal direction of tube 1, which, starting at the furthest distal closure part up toward the furthest proximal closure part, could be sequentially removable from the area of the opening 12 in the circumferential direction of tube 1 in order to expose the opening successively and in steps. Here the closure device would further need to comprise a corresponding actuation mechanism for these closure parts, for example threads guided in bores in the shell wall, which could be pulled back FIGS. 10 to 16 depict a second embodiment of the invention, in which is also provided a closure device 15 disposed rotatably about the longitudinal axis 6 of tube 1. In this embodiment tube 1 is formed such that it is open at its distal end 2. The proximal end of tube 1 is again open and tube 1 is disposed on a mounting portion 7, which includes a hand grip 8 (shown only partially in FIG. 11).

The shell wall 5 encompassing the inner hollow space 4 of tube 1 is formed in the shape of an annulus or a partial annulus. Tube 1 has a (at least substantially) cylindrical section 24 and, in the proximity of the proximal end, a section 25 with increasing circumference (the cylindrical section 24 can also continue within section 25).

Figure 12:
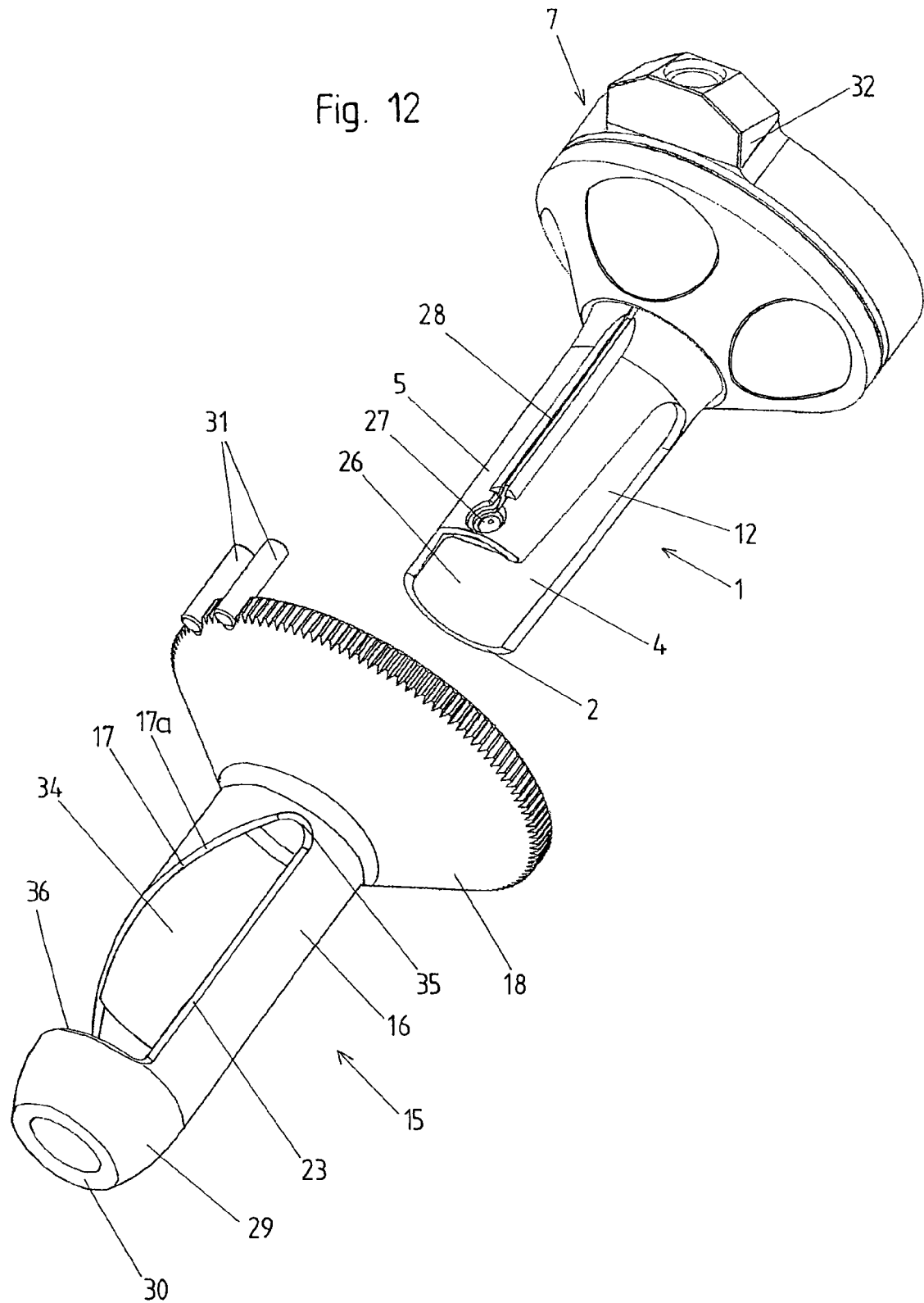
FIG. 12 and FIG. 13 are oblique views from different viewing directions in representation of the tube and the closure device taken apart in exploded view.
Figure 13:
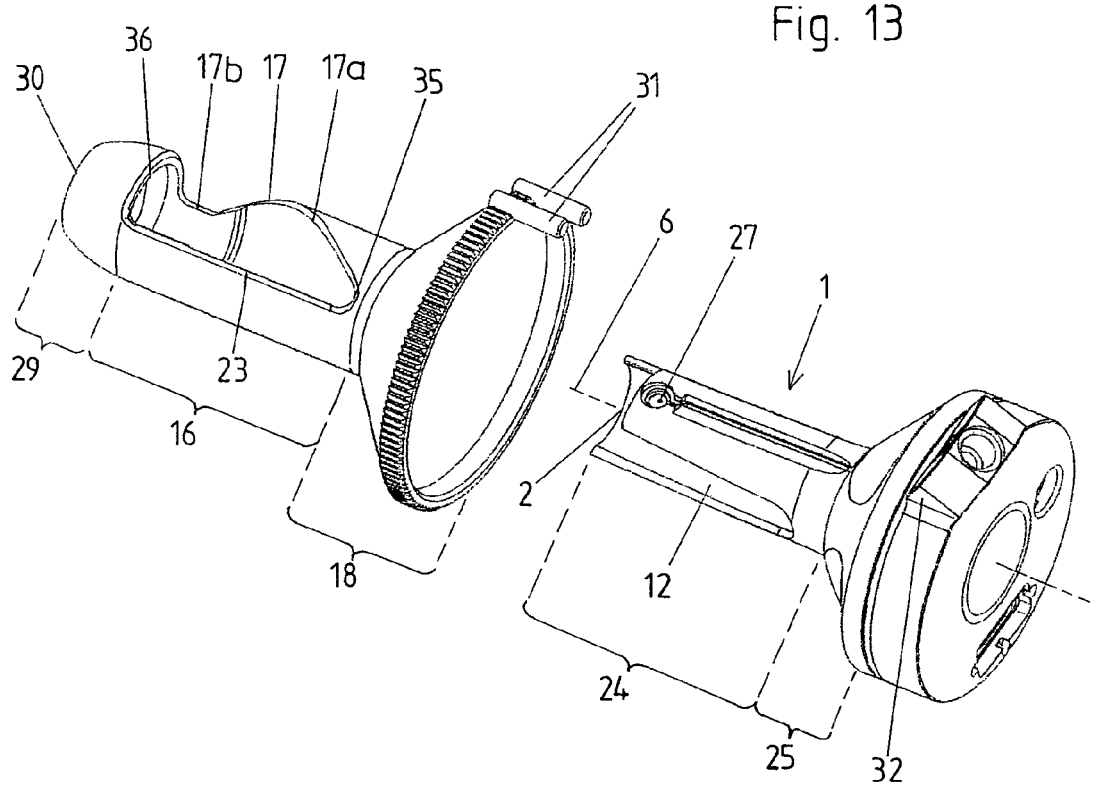

The shell wall 5 of tube 1 has an elongated opening 12 extending in the axial direction of tube 1, which is open toward the distal end 2 of tube 1. The distal end of opening 12 thus coincides with the distal end 2 of tube 1. The proximal end 13 of opening 12 is located in a proximal region of cylindrical section 24. In a region adjoining the distal end 2 of tube 1 the axial opening 12 has a lateral expansion which forms a ligature opening 26. This ligature opening 26 is also open toward the distal end 2 of tube 1. In other words, as shown in FIG. 12, said ligature opening 26 extends laterally from a distal end of said axial (elongated) opening 12 such that said ligature opening 26 and said axial opening 12 form an L-shaped opening.

It would also be conceivable and possible for the axial opening 12 and/or the ligature opening 26 not to extend to the distal end 2 of tube 1 and thus form window openings. Opening 12 and ligature opening 26 can also be separated from one another.

On the shell wall 5 of tube 1 is disposed an ultrasonic sensor 27 which is controlled via an electric line 28 running along the shell wall 5. The ultrasonic sensor 27 is disposed proximally next to the ligature opening 26.

The closure device 15 comprises a closure part 16, which is proximally adjoined by an expanding section 18 with annular cross section. The closure part 16 is distally adjoined by a distal annular section 29, which forms the distal end 30 of the closure device, the section minimally tapering toward the distal end 30 of the closure device 15.

Stop elements 31 cooperating with stops 32, 33 of mounting portion 7 are located on section 18 of the closure device 15.

Closure part 16 is formed in the shape of a portion of the shell of a hollow cylinder. Expressed differently, the closure part 16 is formed in the shape of a hollow cylinder with an opening 34. An edge 17 of this opening has a section 17a, extending helically about the longitudinal axis of the closure part 16, and an axially extending section 17b distally adjoining thereon. Axial edge 23 of opening 34 extends in the axial direction. Section 17a of edge 17 is proximally connected with axial edge 23 via a curved edge 35 of opening 34. Section 17b of edge 17 and edge 23 extend up to the distal end of closure part 16 and are here connected with one another via the proximal edge 36 of section 29 of the closure device.

The circumferential extent of the closure part 16 (thus of the shell of the hollow cylinder which forms the closure part 16) is as large over the axial region, in which the axial opening 12 extends in tube 1, as is the circumferential extent of opening 12 and this circumferential extent of closure part 16 increases toward the proximal end of closure part 16.

In this embodiment the closure device 15 can be placed onto the tube from its distal end 2, and, in the condition of use of the instrument, the closure part 16 encompasses the tube 1 on the outside over a greater or lesser portion of its circumference. The inner diameter of the closure part 16 here corresponds, with the addition of a tolerance to form a slip guide on the tube 1, to the outer diameter of the section of tube 1 encompassed by the closure part 16. The tolerance is best less than 1 mm, a value of less than 0.3 mm being preferred. When the instrument is in use, the tube 1 and the closure 16 are coaxial with respect to one another.

The closure device 15 with the closure part 16 can be rotated with respect to tube 1 about its longitudinal axis or the longitudinal axis of tube 1. To facilitate the rotation, the expanded section 18 includes proximally a corrugated margin. Depending on the rotational position, the following positions are herein assumed:

In the rotational position, in which a stop element 31 of closure device 15 abuts stop 33 of the mounting portion 7, the axial opening 12 in tube 1 is closed by closure part 16, however, the ligature opening 26 in tube 1 is exposed. This position is referred to as "ligature position" (cf. FIGS. 10 and 11).

Figure 14:
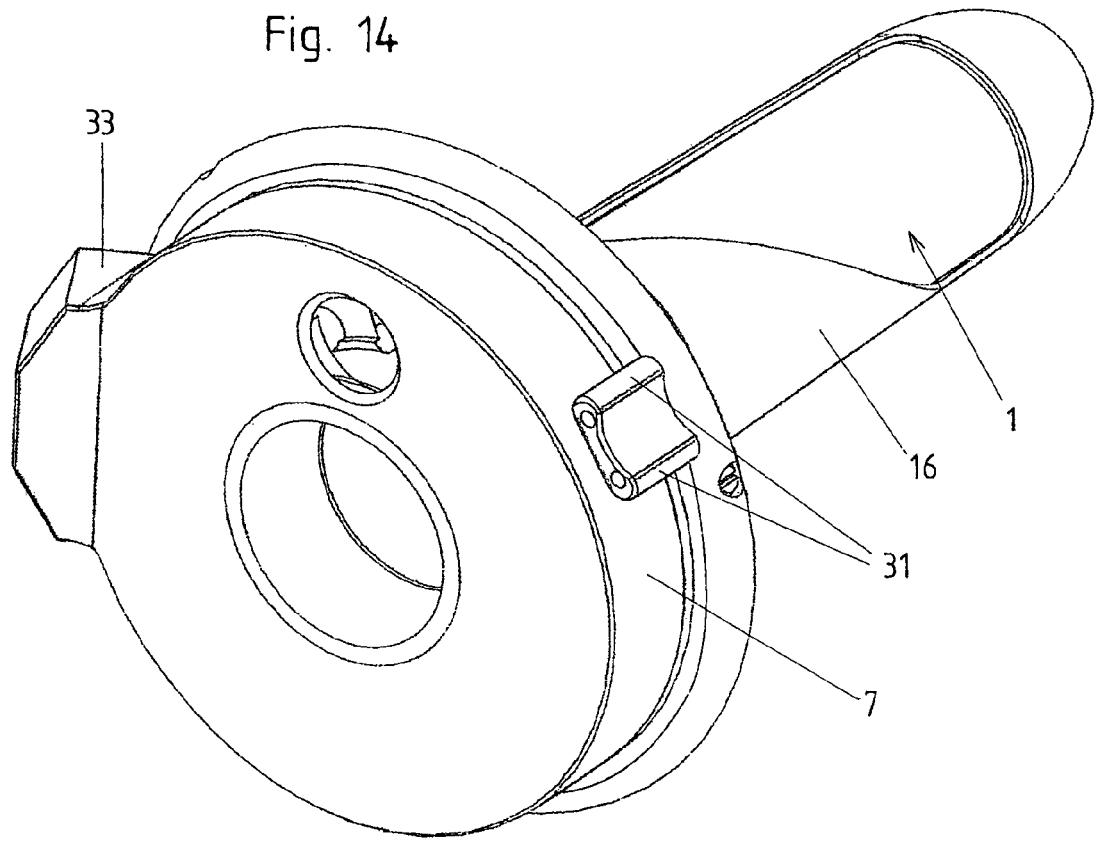
FIG. 14 shows the instrument in the closing position.

In the state of the closure device 15, in which it is completely rotated into the other end position in which a stop element 31 abuts stop 32 of the mounting portion 7, the axial opening 12 as well as also the ligature opening 26 of tube 1 are covered by the closure part 16 and this position is referred to as "closing position". This position is shown in FIG. 14. Section 18 of the closure device is shown in FIG. 14 slightly modified, in particular the two stop elements 31 are formed integrally and the corrugation on the margin is not shown. This applies also to FIG. 15 and FIG. 16.

Figure 15:
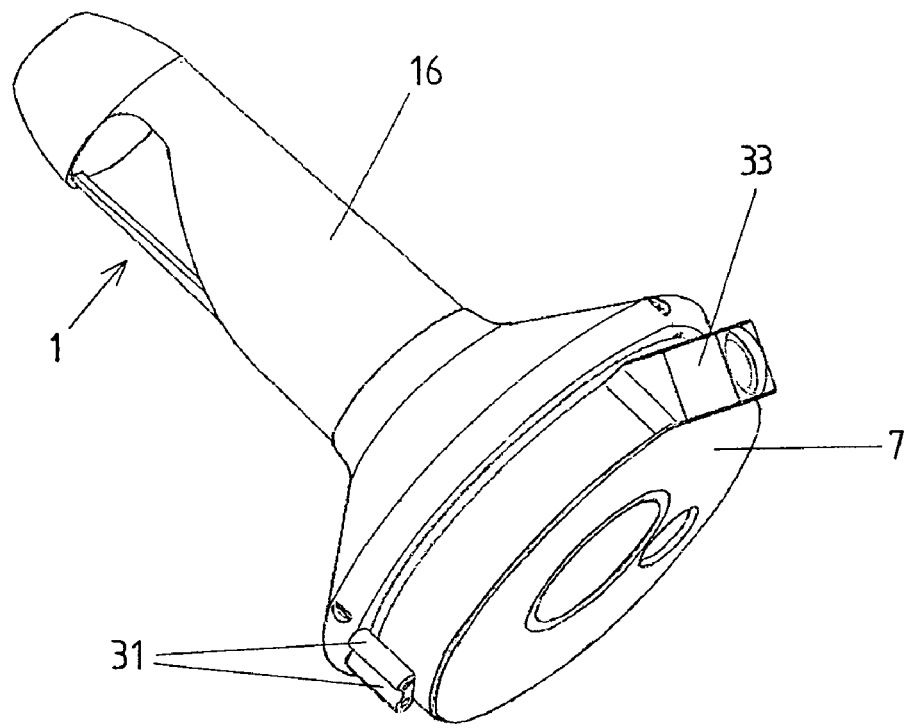
FIG. 15 shows an intermediate position.
Figure 16:
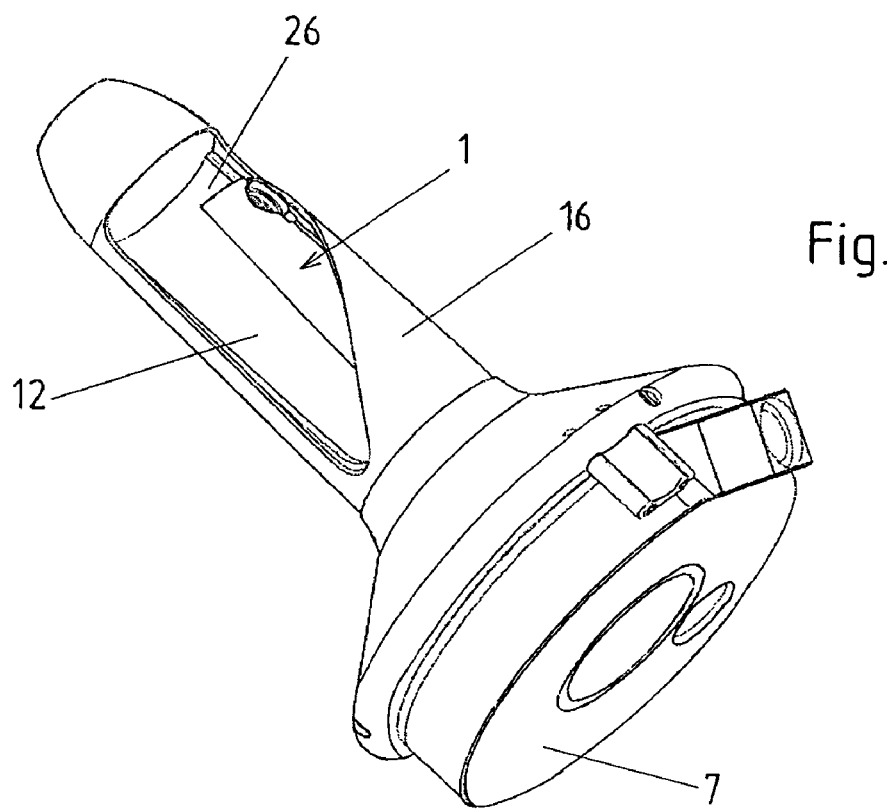
FIG. 16 shows the instrument in the opening position of the closure device, in which the axial opening in the tube is completely exposed.

If, starting from the closing position, the closure device 15 is rotated in the direction toward the ligature position, the axial opening 12 of tube 1 is increasingly exposed in the direction from the distal to the proximal end until it is exposed over its entire length and the "opening position" has been reached (cf. FIG. 16). The positions, in which only a distal section of the axial opening 12 of tube 1 is exposed, are referred to as "intermediate positions". An intermediate position is shown in FIG. 15.

Advantageously, the instrument also comprises in this embodiment again an illuminating device (not shown in FIGS. 10 to 16).

With the instrument depicted in FIGS. 10 to 16 not only a purse-string (continuous, tightening) suture can be applied, but rather the instrument can also be employed for a preceding ligation of hemorrhoid arteries or intramural arteries.

The tube 1 with the parts of the closure device 15 encompassing it on the outside is herein inserted into the rectum and specifically in a rotational position corresponding to the location of a mucosal prolapse to be treated. The closure device is herein in its closing position.

For the subsequent ligation of intramural (=located in the intestinal wall) arteries the closure device is rotated into the ligature position. The ligature is herein performed in the conventional manner by locating the corresponding arteries by means of the ultrasonic sensor (and the appropriate control and analysis electronic circuitry) through the ligature opening 26 in order to reduce the blood supply to the "cavernosum recti".

By rotating the closure device, the axial opening 12 is subsequently exposed stepwise starting at its distal end 14, with the surgeon applying a continuous suture (in the manner already described). This suture grasps the mucosa, the submucosa and possibly also the "muscularis mucosae". With a thin needle holder and appropriately curved needle, the suture is applied through the inner hollow space 4 of tube 1. The continuous suture is applied stepwise over a length of 4 to 6 cm up into the proximity of the dentate line. By tying the continuous suture into the distal rectum a repositioning (or lifting) and fixing of the mucosa prolapse takes place and an anatomical reconstruction of the corpus cavernosum recti.

After tying the continuous suture in the proximity of the distal end 14 of the axial opening 12, the instrument is removed from the rectum, the closure device 15 is brought into the closing position and the instrument is again inserted in order to treat the next prolapsed mucosal prolapse in the same manner. This is repeated until all mucosal prolapses over the circumference of the rectum have been treated.

It is also possible for the surgeon to guide an instrument through the open distal end of the instrument according to the invention during the operation and to push with this inserted instrument the prolapsed mucosa in the distal direction in order to aid the purse-stringing and to relieve the suture of stress.

A formation of the tube 1 closed at the distal end and/or of the closure device 15 is conceivable and possible, however, it is less preferred.

For a defined setting of the rotational positions of the closure device 15 a snap device can be provided acting between the mounting 7 and the closure device 15.

As is evident in the above description, the scope of the invention is not limited to the depicted embodiments, but rather, should be determined with reference to the attached claims together with the full range of possible equivalents. While the above description and the drawings illustrate the invention, it is obvious to a person of skill in the art that different modifications can be carried out therein without going beyond the true spirit and scope of the invention.

LEGEND TO THE REFERENCE NUMBERS 1 tube
2 distal end of the tube
3 proximal end of the tube
4 inner hollow space of the tube
5 shell wall of the tube
6 longitudinal axis
7 mounting
8 hand grip
9 flange
10 part
11 cap nut
12 opening of the tube
13 proximal end of the opening
14 distal end of the opening
15 closure device
16 closure part
17 edge
17a section of edge
17b section of edge
18 section of closure device
19 annular flange
20 handle
21 light-emitting diode
22 cable
23 edge
24 cylindrical section of the tube
25 section of the tube
26 ligature opening
27 ultrasonic sensor
28 electric line
29 distal section
30 distal end of the closure device
31 stop element
32 stop
33 stop
34 opening in the closure part
35 edge
36 edge

The invention claimed is:

1. An instrument for use in the treatment of a prolapsed hemorrhoid, comprising:
a tube having:
a distal end to be inserted into the rectum of a patient;
an open proximal end; and
a shell wall encompassing an inner hollow space, said shell wall having an elongated opening extending in an axial direction of said tube, a ligature opening at said distal end of said tube, and a cylindrical section located between said distal end and said proximal end, said cylindrical section forming the largest portion of a longitudinal extent of said tube, said ligature opening being connected to a distal end of said elongated opening and extending laterally from said distal end of said elongated opening such that said ligature opening and said elongated opening form an L-shaped opening;
a closure device for closing and opening said elongated opening of said tube, said closure device comprising a closure part formed of a hollow cylinder shell portion, said closure part being rotatable with respect to said tube about a longitudinal axis of said tube, said closure part being arranged within said tube or such that said tube is arranged within said closure part, so as to continuously and successively expose said elongated opening in a direction from said distal end of said tube to said proximal end of said tube as said closure part is rotated with respect to said tube to thereby receive the prolapsed hemorrhoid within said tube; and
an ultrasonic sensor on said tube located adjacent to said ligature opening and at a side of said ligature opening closest to said proximal end of said tube, and spaced apart from a lateral side of said elongated opening.

2. The instrument of claim 1, wherein said closure part is arranged within said tube such that a tolerance for a slip guide in said tube is formed between an outer diameter of said closure part and an inner diameter of a section of said tube encompassing said closure part.

3. The instrument of claim 1, wherein said tube is arranged within said closure part such that a tolerance for a slip guide on said tube is formed between an inner diameter of said closure part and an outer diameter of a section of said tube encompassed by said closure part.

4. The instrument of claim 1, wherein a section of said closure part at an axial position corresponding to said elongated opening of said tube has a width at least as big as a width of said elongated opening, wherein said elongated opening of said tube is completely closed by said section of said closure part in one rotational position of said closure part with respect to said tube.

5. The instrument of claim 1, wherein said closure part has an oblique first edge extending helically about a center longitudinal axis of said closure part.

6. The instrument of claim 5, wherein said closure part has an axial second edge extending parallel to the center longitudinal axis of said closure part.

7. The instrument of claim 6, wherein each of said oblique first edge and said axial second edge originate at the same point adjacent to a proximal end of said closure part, and extend outward from the same point such that a distance between said oblique first edge and said axial second edge increases evenly toward a distal end of said closure part.

8. The instrument of claim 1, further comprising a mounting portion including a hand grip, said tube being attached to said mounting portion.

9. The instrument of claim 1, further comprising an illuminating device for illuminating an operating area.

10. The instrument of claim 9, wherein said illuminating device includes an LED for emitting light into an end of said tube, said shell wall of said tube being translucent so as to allow the light emitted by said LED to pass therethrough.

11. The instrument of claim 1, further comprising a stop for delimiting the
insertion of said tube into the rectum.

12. The instrument of claim 1, wherein said tube has a length in a range of 60 mm to 100 mm.

13. The instrument of claim 1, wherein said elongated opening of said shell wall has an axial length in a range of 40 mm to 80 mm.

14. The instrument of claim 1, wherein said elongated opening of said shell wall has a width, measured at right angles to the longitudinal axis of said tube, in a range of 8 mm to 20 mm.

15. The instrument of claim 1, wherein said ligature opening of said shell wall is opened and closed by said closure device.

16. The instrument of claim 1, wherein a distal end of said ligature opening and said distal end of said elongated opening are open.

17. A method for the treatment of a prolapsed hemorrhoid by applying a continuous suture to the hemorrhoid, said method comprising:

inserting a tube into the rectum of a patient, the tube having a distal end to be inserted first into the rectum, an open proximal end, and a shell wall encompassing an inner hollow space, the shell wall having an elongated opening extending in an axial direction of the tube, the elongated opening being closed until the tube is fully inserted by a closure device set in a closing position;

after said inserting of the tube, exposing a distal first section of the elongated opening in the tube by moving the closure device an initial amount towards an opening position of the closure device;

after said exposing the distal first section of the elongated opening, applying a first stitch of the continuous suture to a portion of the hemorrhoid which has prolapsed into the exposed first section of the elongated opening;

after said applying the first stitch, exposing a second section of the elongated opening which is closer to the proximal end of the tube than the first section, by moving the closure device a further amount towards the opening position; and after said exposing the second section of the elongated opening, applying a second stitch of the continuous suture to a portion of the hemorrhoid which has prolapsed into the exposed second section of the elongated opening.

18. The method of claim 17, further comprising:

repeatedly exposing additional sections of the elongated opening closer to the proximal end of the tube by moving the closure device further towards the opening position until the closure device is in the opening position and the entire elongated opening is exposed; and after each additional section of the elongated opening is exposed, applying a stitch in a portion of the hemorrhoid which has prolapsed into the additional section of the elongated opening until a desired number of stitches has been applied to the hemorrhoid as the continuous suture; and tying the continuous suture so as to lift the prolapsed hemorrhoid into the anal canal of the patient.

19. The method of claim 18, further comprising:

before said exposing of the distal first section of the elongated opening, locating a hemorrhoidal artery using an ultrasonic sensor on the tube, the tube having a ligature opening adjacent to the ultrasonic sensor; and before said applying the first stitch, applying a hemorrhoid arterial ligature to the hemorrhoidal artery via the ligature opening.

20. The method of claim 17, further comprising:

before said exposing of the distal first section of the elongated opening, locating a hemorrhoidal artery using an ultrasonic sensor on the tube, the tube having a ligature opening adjacent to the ultrasonic sensor; and before said applying the first stitch, applying a hemorrhoid arterial ligature to the hemorrhoidal artery via the ligature opening.

21. The instrument of claim 1, wherein said tube and said closure device are configured and connected so as to be arrangeable in:

a first position wherein said elongated opening and said ligature opening of said tube are both completely closed by said closure part;

a second position wherein said elongated opening is completely closed by said closure part and said ligature opening is completely open;

a third position wherein said elongated opening and said ligature opening are both completely open; and a fourth intermediate position wherein said ligature opening is completely closed by said closure part and only a proximate section of said elongated opening is closed by said closure part while a remaining distal section of said elongated opening is open.

* * * * *